United States Patent [19]
Brandt

[11] Patent Number: 5,496,716
[45] Date of Patent: Mar. 5, 1996

[54] STABILIZED CREATIVE KINASE MB COMPOSITION

[75] Inventor: Douglas R. Brandt, Mundelein, Ill.

[73] Assignee: Abbott Laboratories, Abbott Park, Ill.

[21] Appl. No.: 240,794

[22] Filed: May 10, 1994

Related U.S. Application Data

[63] Continuation of Ser. No. 973,604, Nov. 9, 1992, abandoned, which is a continuation of Ser. No. 429,591, Oct. 31, 1989, abandoned.

[51] Int. Cl.$^6$ .............................. C12N 9/96; C12N 9/12; C12Q 1/50; G01N 33/53
[52] U.S. Cl. .............................. 435/188; 135/7.1; 135/17; 135/194
[58] Field of Search .............................. 435/7.1, 17, 188, 435/194

[56] References Cited

U.S. PATENT DOCUMENTS

| | | | |
|---|---|---|---|
| 3,556,945 | 1/1971 | Messing | 195/63 |
| 4,310,625 | 1/1982 | Modrovich | 435/17 X |
| 4,652,524 | 3/1987 | Modrovich et al. | 435/188 |
| 4,888,289 | 12/1989 | Takami et al. | 435/17 X |
| 4,931,392 | 6/1990 | Rehner et al. | 435/188 |
| 4,994,375 | 2/1991 | Posner et al. | 435/188 X |

FOREIGN PATENT DOCUMENTS

| | | | |
|---|---|---|---|
| 0045122 | 2/1982 | European Pat. Off. | 435/17 |
| 00116307 | 8/1984 | European Pat. Off. | C12Q 1/50 |

OTHER PUBLICATIONS

J. Grant, *Hackh'Chemical Dictionary*, Third Edition, McGraw—Hill Book Co., New York, NY, p. 54.
Biochemicals Organic Compounds for Research and Diagnostic Reagents, 1991 Sigma Chemical Company Catelog, p. 1709.
V. Whitner et al., "Stability of Creatine Kinase-3 Lyophilized Materials", *Clinical Chemistry*, vol. 28/1 (1982), pp. 41–44.
*Chemical Abstracts*, vol. 100, No. 25, Jun. 1984 Columbus Ohio, USA, p. 256; left–hand column; ref. No. 205712p. (Abstract & JA–A–5921390 [Mitsubishi Petrochemical Co., Ltd]0 3 Feb. 1984.).
R. D. Schmid, "Stabilized Soluble Enzymes", *Advances in Biochemical Engineering*, vol. 12 (1979), p. 57, line 11–p. 59, line 2.

*Primary Examiner*—David M. Naff
*Attorney, Agent, or Firm*—Lawrence S. Pope

[57] ABSTRACT

A stabilized liquid enzyme composition is prepared containing at least one enzyme substrate or analog thereof and/or at least one enzyme product or analog thereof combined with the enzyme in a liquid medium containing. The liquid medium may be human, animal or artificial serum. The composition may also contain an activator chosen from a sulfhydryl compound and a divalent metal ion. In a preferred embodiment, the enzyme is isolated creatine kinase MB(CKMB), the substrate may be adenosine triphosphate, its oxidized or analog form, creatine or its analog, and the product may be adenosine diphosphate, its oxidized or analog form or phosphocreatine or its analog. The activator is preferably N-acetyl-cysteine or β-mercaptoethanol. In a preferred embodiment, CKMB is stabilized with a combination of adenosine triphosphate and creatine. A preferred serum is heat-inactivated alkaline-shocked human serum. The composition displays less than 10% loss of CKMB isoenzyme concentration after 27 days storage at room temperature as measured by an immunoassay. The composition is useful as a calibrator or control reference in an immunoassay.

10 Claims, 1 Drawing Sheet

STABILIZED CREATIVE KINASE MB COMPOSITION

This application is a continuation of U.S. patent application Ser. No. 07/973,604 filed Nov. 9, 1992, now abandoned, which in turn is a continuation of U.S. patent application Ser. No. 07/429,591, filed Oct. 31, 1989, now abandoned.

BACKGROUND OF THE INVENTION

1. Field of the Invention

This invention relates to the stabilization of enzymes. In particular, the invention relates to stabilized enzyme compositions containing creatine kinase isoenzymes for use in diagnostic assays.

2. Description of Related Art

Following ischemic damage to cardiac tissue, a large quantity of enzymes are released into the blood stream. The detection of the presence or increased quantity of one or more of these enzymes is routinely used to confirm that an acute myocardial infarction has occurred. Three principle enzymes are used for this purpose: creatine kinase (CK), also referred to as creatine phosphokinase, serum glutamic oxaloacetic transaminase (SGOT), and lactate dehydrogenase (LDH). The rates of release of these enzymes differ, and the temporal pattern of release is of diagnostic importance. The CK level in serum begins to rise within four to six hours after the onset of chest pain. A peak CK level is seen between 12 and 24 hours, and then the level rapidly returns to the normal range within 72 to 96 hours. In comparison, peak serum levels of SGOT occur at 24 to 48 hours, and peak LDH levels occur after two to four days. Thus, the detection of increased amounts of the CK enzyme in the blood provides an early indication of myocardial infarction.

Creatine kinase is a dimer, composed of the M and B subunits which give rise to three predominant creatine kinase isoenzymes present in human tissues. The CKBB isoenzyme (or $CK_1$) is present predominantly in brain and intestinal tissue. The CKMB isoenzyme (or $CK_2$) is present predominantly in heart muscle and in the diaphragm and esophagus (smooth muscle). The CKMM isoenzyme (or $CK_3$) is present in all tissues, and especially in skeletal muscle. The CKMB isoenzyme is not unique to cardiac tissue, nor is it the predominant CK isoenzyme present in cardiac tissue. As a percentage of total CK, however, the heart contains more CKMB than do other tissues. Therefore, in the absence of major muscle trauma, the appearance of CKMB in serum is used as a clinical indication of cardiac damage.

The prompt analysis of the CKMB level for the diagnosis of acute myocardial infarction has important therapeutic and economic implications. Many patients with chest pain are admitted to coronary care units and subjected to extensive and expensive evaluations. If the analysis for CKMB in serum or plasma indicates no elevation in the CKMB level for 12 to 24 hours following chest pain, the patient can be transferred from the intensive care unit.

Because differentiation between the isoenzymes of CK is clinically important, efficient and discriminatory assays for these isoenzymes are desirable. Several different methods are conventionally used for separating and measuring CK isoenzymes. Electrophoresis and column chromatography methods, which are typically used, physically separate the isoenzymes which can then be measured. However, both the electrophoretic and the column chromatographic assays are time consuming and require considerable skill.

Other analytical methods useful in the measurement of CK isoenzymes are immunoinhibition and immunoassays. These methods rely upon the interaction of CK isoenzymes and CK isoenzyme-specific antibodies. Such methods can be automated or configured to include disposable devices, thereby decreasing user time and the need for training, and increasing the speed and facility with which the assays are performed.

Typically, enzyme preparations containing known amounts of an enzyme are provided in diagnostic kits as reference samples to assure the accuracy and consistency of the assay results. For example, with an automated CKMB immunoassay, CKMB isoenzyme preparations of varying concentration can be provided for use as instrument calibrators and/or controls. To provide precision and uniformity among separate assays when conducted over a period of time, the enzyme preparations must be stable. However, because enzymes such as the CK isoenzymes are heat labile, they must be stabilized.

Conventional techniques for stabilizing an enzyme preparation include formulating the enzyme into a solid matrix by freeze-drying or lyophilizing the reagent to form a reconstitutable powder or tablet. These techniques have disadvantages. In freeze-drying, the water is removed, thereby relinquishing part of the quality control cycle to the user's dilution and reconstitution of the reagent. Other disadvantages of freeze-dried enzyme reagents include: variable irreversible inactivation during freeze-drying, and a time and/or temperature-dependent reactivation phase. In addition, freeze-dried enzyme preparations may have a relatively short stability, once reconstituted. Currently available commercial enzyme immunoassay kits containing the CKMB isoenzyme typically provide freeze-dried calibrator and control reference reagents which are stable at 2°–8° C. for 7–14 days after reconstitution.

Other attempts at stabilizing enzymes involve binding the enzymes to organic carrier materials such as cellulose particles, or binding the enzyme to an inorganic carrier material with reactive silanol groups as described by Messing, U.S. Pat. No. 3,556,945. Alternatively, Modrovich et al. (U.S. Pat. No. 4,652,524) describe the covalent binding of enzymes (e.g., creatine kinase) to pendant groups on carrier polymers, such as polyacrylic acid and polymethacrylic acid, to stabilize the enzyme. These methods require complex production steps, and the binding of the enzyme to the carrier can inhibit the activity of the enzyme. The addition of adenosine diphosphate to stabilize CKMM isoenzyme is disclosed in Whitner, et al., Clinical Chemistry, 28[1], 41–44, 1982.

SUMMARY OF THE INVENTION

The present invention provides stabilized enzyme compositions. The compositions include a predetermined amount of the enzyme to be stabilized, and an enzyme substrate, combined in a liquid medium. The enzyme is in an unmodified form, i.e., it is not bound or complexed to a carrier material or a polymer particle. The liquid medium is selected from human, animal or artificial serum, and can include a buffer. Optionally, the stabilized enzyme composition can include one or more other enzyme substrates, enzyme products or analogs thereof. Furthermore, the stabilized enzyme composition can optionally include an enzyme activator.

The present invention also provides methods for preparing stable diagnostic enzyme reagents useful in CKMB assays. The present invention also includes kits of reagent solutions for use as calibrators and/or controls in CKMB assays.

DETAILED DESCRIPTION OF THE INVENTION

Figure 1:
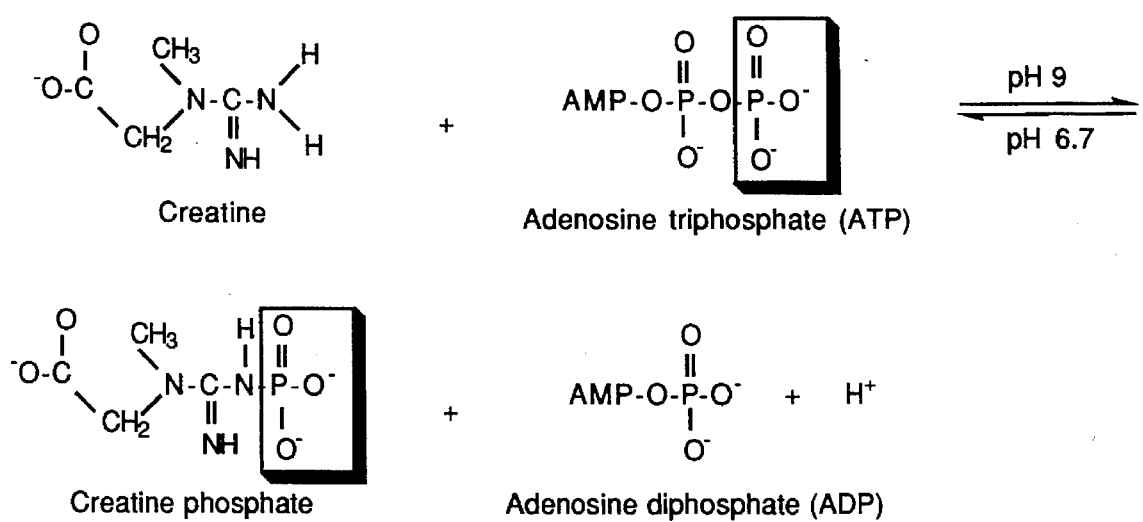
FIG. 1 depicts the catalytic reaction of enzyme substrates and enzyme products by creatine kinase.

In accordance with the invention, it has been discovered that enzymes can be stabilized efficiently and effectively by formulating an enzyme composition by mixing the enzyme with an enzyme substrate, an enzyme substrate and enzyme product, or a pair of enzyme products in a liquid media. Optionally, the stabilized enzyme composition can include one or more other enzyme substrates, and an enzyme activator. In addition, enzyme substrate analogs and enzyme product analogs can be used.

DEFINITIONS

The following definitions are used herein.

The term "stabilized", as used herein, refers to the protection of an enzyme's catalytic or reactive ability by preventing or decreasing the inactivation of the enzyme for a period sufficient for typical shipment, storage and use.

The term "catalyst", as used herein, means a substance which increases the rate of a particular chemical reaction without itself being consumed or permanently altered and without altering the equilibrium constant of the chemical reaction. At the end of a catalyzed reaction, the catalyst is substantially unchanged and the reaction materials have undergone transformation into new products.

The term "substrate", as used herein, means a substance upon which an enzyme acts.

The term "product", as used herein, means a substance formed by the reaction of an enzyme on a substrate.

The term "activator", as used herein, means reducing agents, divalent metal ions and mixtures thereof. Suitable divalent metal ions include, but are not limited to, magnesium, manganese, calcium and cobalt. Suitable reducing agents include, but are not limited to, sulfhydryl compounds such as mercaptoethanol, cysteine, N-acetylcysteine (NAC), dithioerythritol, S-(2-aminoethyl)isothiouronium bromide hydrobromide, glutathione, thioglycollic acid, dithiothreitol and analogs or equivalents thereof. Sulfhydryl binding reagents inhibit enzyme activity as a result of sulfhydryl oxidation or internal disulfide formation. Substantially full reactivity can be restored to the enzyme by incubating the enzyme with an activator, such as a sulfhydryl compound. Especially preferred activators include β-mercaptoethanol and NAC.

In accordance with the present invention, the production of advantageous enzyme reagent solutions is made possible. Such reagent solutions contain a known quantity of enzyme, and the reactive ability of the enzyme has been found to be stable for a prolonged period. The present invention provides for the stabilization of such enzyme reagent solutions by including the enzymes of interest within a reagent matrix comprising one or more enzyme substrates and/or enzyme products. In addition, a reagent matrix of the present invention can include one or more enzyme activators. The present invention thus accomplishes the stabilization of an unmodified enzyme, i.e., an enzyme that is not immobilized upon an organic or inorganic carrier and that is not covalently bound to a polymer.

While the present invention, as described in the Specification, has been demonstrated as successful with the creatine phosphate model, it will be appreciated that virtually any enzyme can be stabilized by one skilled in the art by employing the teaching herein, provided that the necessary routine changes in substrates and/or products are made and testing performed. Accordingly, the concepts and techniques described herein can be used to stabilize, for example, lipases, peroxidases, transaminases, phosphatases, dehydrogenases, glycosidases, lactamases, etc., with the selection and addition of the appropriate substrates and/or products for a given enzyme.

Suitable enzymes which can be stabilized in accordance with the present invention can be classified under three general headings: hydrolytic enzymes, redox enzymes, and transferase enzymes. The hydrolytic enzymes include proteolytic enzymes which hydrolyze proteins, carbohydrates, esters, nucleases and amines. The redox enzymes catalyze oxidation or reduction reactions. The transferase enzymes transfer groups from one molecule to another. In particular, specific enzymes which may be stabilized by the reagent matrixes of the invention are presented in Table 1; suitable enzyme substrates and enzyme products for making the stabilized enzyme compositions are also presented.

TABLE 1

| ENZYMES | SUBSTRATES | PRODUCTS |
| --- | --- | --- |
| Alkaline phosphatase | ● nitrophenylphosphate<br>● alkylphosphate<br>● allylphosphate<br>● phenylphosphate | |
| Lactate dehydrogenase | ● lactate<br>● nicotinamide-adenine dinucleotide | ● pyruvate<br>● nicotinamide-adenine dinucleotide, reduced |
| Phospholipase A2 | ● phosphatidyl choline | |
| Aspartate transaminase | ● aspartate<br>● alpha-ketoglutarate | ● oxaloacetate<br>● glutamate |
| Beta-glucuronidase | ● carbohydrate with terminal glucose component | |
| Ribonuclease 1 | ● ribonucleic acids with 3' linkage of pyrimidine nucleotide | |
| Beta-lactamase | ● penicillins<br>● cephalosporins | |
| Horseraddish peroxidases | ● pyrogallol | |
| Hexokinase | ● glucose<br>● adenosine triphosphate | ● glucose-6-phosphate dehydrogenase<br>● nicotinamide-adenine dinucleotide, reduced |
| Creatine kinase | ● creatine<br>● adenosine triphosphate | ● creatine phosphate<br>● adenosine diphosphate |

Suitable liquid media useful in the invention for the formulation of a reagent matrix include normal human serum (NHS), normal horse serum and normal goat serum. Any convenient liquid medium can be used in which the enzyme and other components of the composition are soluble or in which they can be solubilized, including physiological diagnostic base, bovine serum albumin (BSA), bovine gamma globulin (BGG), artificial serums and protein solutions (i.e., solutions designed to mimic serum solutions.) The choice of a specific liquid medium by the routineer will depend upon the acceptable performance of that particular medium in the diagnostic assay. For example, acceptable performance characteristics of the liquid medium include, but are not limited to, the appropriate recovery of the enzyme that is added to the medium, the absence of precipitates subsequent to long term storage, and the absence of substances which might interfere with the assay.

Creatine kinase was chosen as a model enzyme due to its frequent use in assays. For example, solutions of the CKMB isoenzyme are often used as reference reagents (i.e., assay calibrators and controls) in a CKMB assay. It is desirable that such enzyme reagents not be heat-inactivated during shipment, storage or normal use.

Creatine is a compound synthesized in the body as a precursor to an important storage form of high-energy phosphate. Creatine kinase is the enzyme catalyst for the reaction in which high-energy creatine phosphate is formed by catalyzing the reaction between creatine and adenosine triphosphate. As shown in the reaction sequence of FIG. 1, both creatine and adenosine triphosphate (ATP) are substrates in the formation of the products adenosine diphosphate (ADP) and creatine phosphate, which is also referred to as phosphocreatine. Adenosine monophosphate is represented as AMP.

In preparing a stabilized creatine kinase composition according to the present invention, the enzyme substrate additives are chosen from ATP or ATP analogs, such as adenosine-5'-0(3-thiotriphosphate), adenylyl-imidodiphosphate and adenylyl-($\beta,\Upsilon$-methylene)diphosphate. Oxidized ATP can be used, as can an oxidized ATP analog or another ATP affinity analog which irreversibly binds to the active site of the CK isoenzyme to stabilize the molecule. The stabilized creatine kinase composition can optionally include a second enzyme substrate in the form of creatine or creatine analogs such as $\beta$-guanidinopropionic acid, 1-carboxymethyl-2-iminoimidazolidine creatinine, N-methyl-3-guanidinopropionate, N-amidino-N-ethylglycine, 1-carboxyethyl-2-iminoimidazolidine and N-(2,3-epoxypropyl)-N-amidinoglycine.

Furthermore, combinations of enzyme substrate and enzyme product, such as a creatine/ADP combination or an ATP/phosphocreatine combination, can be used in the stabilized reagent matrix. The enzyme products are chosen from creatine phosphate, ADP and their analogs. The ADP analogs include, but are not limited to, adenosine-imidodiphosphate, adenosine-5'-0(2-thiodiphosphate) and adenylyl-($\alpha,\beta$-methylene)diphosphate. Oxidized ADP can be used, as can oxidized ADP analogs or other ADP affinity analogs. The phosphocreatine analogs include but are not limited to, 1-carboxymethyl-2-imino-3-phosphonoimidazolidine phosphocreatine, N-methyl- 3-guanidinopropionate phosphate, N-amidino-N-ethylglycine phosphate, 1-carboxyethyl- 2-imino-3-phosphonoimidazolidine phosphocreatine, N-methyl-N-($\beta$-hydroxyethyl)guanidine and O-phosphate (creatinol O-phosphate).

Heat-inactivation of certain liquid media, for example normal human serum solutions, is desirable to prevent the possible precipitation of serum proteins upon the addition of ATP to the reagent matrix. It is believed that the inclusion of ATP in serum results in the phosphorylation of serum proteins and the subsequent precipitation of those proteins from solution. Because ADP can be enzymatically converted to ATP via adenylate kinase, ADP can also cause precipitates in a serum medium. While low levels of ATP or ADP might not result in the formation of precipitates, heat inactivation of the liquid medium is typically performed in the preparation of a stabilized creatine kinase isoenzyme reagent matrix.

In addition, it is desirable to alkaline-shock certain liquid media, such as normal human serum solutions, to prevent non-ATP dependent precipitation of serum proteins over time. It is believed that alkaline shocking results in the hydrolysis of lipoproteins into their lipid and protein components which have greater long term solubility. Non-serum based liquid media, such as bovine albumin solutions, need not be alkaline shocked.

A liquid medium formulated according to the invention can be buffered with any suitable buffering agent providing a reagent matrix pH of from about 6 to about 9. Possible buffering agents include, but are not limited to, tris(hydroxymethyl)aminomethane (Tris), 2-(N-morpholino)ethanesulfonic acid (MES), and N-( 2-hydroxyethyl)piperazine-N'-(2-ethane sulfonic acid) (HEPES).

In the case of CKMB enzyme reagent stabilization, ATP and creatine are the preferred substrate additives. The amount of ATP used is preferably a concentration which provides saturation binding of ATP to CKMB. An ATP concentration of about 0.1 millimoles (mM) to about 100 mM can be used. An ATP concentration of about 0.5 mM to about 50 mM is preferred, and a concentration of about 2.0 mM to about 10 mM is most preferred. The amount of creatine used in the reagent matrix ranges from a concentration of about 1.0 mM to about 200 mM. A creatine concentration of about 5.0 mM to about 160 mM is preferred, and a concentration of about 15 mM to about 50 mM is most preferred. If the CKMB reagent matrix also contains an enzyme product, such as ADP, the useful ADP concentration ranges are comparable to that of ATP, and the useful creatine phosphate concentration ranges are comparable to that of creatine. One example of a reagent matrix includes normal human serum, which is heat-inactivated (56° C. for one hour) and alkaline-shocked (pH 11 at 2°–8° C. for three days followed by adjustment to pH 8.0 and filtration), containing 5 mM ATP, 30 mM creatine, 0.2% sodium azide and 20 mM NAC. Such stabilized enzyme reagent compositions prepared in accordance with the present invention have displayed less than a 10% loss of CKMB concentration after five months at 2°–8° C., or after 27 days at room temperature.

The reagents stabilized by the methods provided by the present invention are readily used in diagnostic assays as calibrator and control reference reagents in enzyme assays, and the resulting enzyme reagent solutions provide several advantages over other commercially available enzyme assay reference reagents. The stabilized enzyme compositions have a relatively long shelf-life and retention of activity as compared to conventional enzyme reagent preparations. When stored at room temperature over a period of weeks, the enzyme reagent compositions of the present invention exhibit a substantially constant level of enzyme activity following repeated exposure to assay conditions. The reagents can also be frozen to further enhance storage capabilities. The invention is further illustrated by the following examples.

EXAMPLES

The examples describe methods for synthesizing the novel enzyme compositions of the present invention as well as experiments which were performed to determine their stability. Table 2 illustrates some of the different enzyme reagent compositions which were produced in accordance with the invention as specifically described in the following examples.

TABLE 2

CK Enzyme Reagent Matrixes

| Matrix | NHS* | NAC** | ATP | ADP | Creatine | Phosphocreatine |
|---|---|---|---|---|---|---|
| A | + | + | + |   | + |   |
| B | + |   | + |   | + |   |
| C | + | + |   | + | + |   |
| D | + |   |   | + | + |   |
| E | + | + | + |   |   | + |
| F | + |   | + |   |   | + |
| G | + | + |   | + |   | + |
| H | + |   |   | + |   | + |

*NHS = normal human serum
**NAC = N-acetyl-cysteine

EXAMPLE 1

Normal Human Serum Medium with N-Acetyl-Cysteine

Reagent matrix-A was made using the following procedure. Normal human serum (Gibco; Grand Island, N.Y.) was heat inactivated at 56° C. for one hour. The NHS liquid medium was then cooled to room temperature, adjusted to pH 11.0 with sodium hydroxide, and stored at 2°–8° C. for one to five days. When removed from storage, the medium was adjusted to pH 8.0 with hydrochloric acid. The following reagents (Sigma) were then added to complete the reagent matrix: ATP (5 mM) and creatine (30 mM) as two CK enzyme substrates; sodium azide (0.2%) as a preservative; and NAC (20 mM) as an activator. The reagent matrix was sterile-filtered through a final pore size of 0.22 micrometers and was frozen until used.

EXAMPLE 2

Normal Human Serum Medium without N-Acetyl-Cysteine

Reagent matrix-B was prepared substantially in accordance with the procedure described in Example 1, with the exception that NAC was omitted from the matrix.

EXAMPLE 3

Normal Human Serum Medium with ADP

Reagent matrixes C and D were prepared substantially in accordance with the procedures described in Examples 1 and 2, with the exception that ADP (5 mM, Sigma) was substituted in place of ATP, thereby producing matrixes containing both an enzyme substrate and an enzyme product.

EXAMPLE 4

Normal Human Serum Medium with Phosphocreatine

Reagent matrixes E through H were prepared substantially in accordance with the procedures described in Examples 1, 2 and 3, with the exception that phosphocreatine (30 mM, Sigma) was substituted in place of creatine.

EXAMPLE 5

Reagent Matrixes with Non-NHS Liquid Media

Reagent matrixes were prepared substantially in accordance with the procedures described in Examples 1, 2, 3 and 4, with the exception that an animal, artificial serum or artificial protein solution was substituted in place of the normal human serum. Animal serums which were used included normal horse serum and normal goat serum. Artificial serums included physiological diagnostic base (Armour; Tarrytown, N.Y.), BSA and BGG.

EXAMPLE 6

Creatine Stabilization of CKMB Reagent Solution

Reagent matrixes were prepared substantially in accordance with the procedures described in Examples 2 and 3 wherein NAC was omitted from the matrix and wherein either ADP or ATP was present in the matrix (as shown in Table 2, reagent matrixes B and D.) Two similar reagent matrixes were then prepared with the exception that creatine was omitted from the matrix. A fifth reagent matrix was prepared which omitted creatine, ATP and ADP, i.e., the matrix contained only NHS, NAC and sodium azide. On day zero, a known amount of purified CKMB isoenzyme (Aalto; Escortdido, Calif.) was added to the five different reagent matrixes. Subsequent to storage at room temperature, the CKMB concentration of each matrix was periodically quantitated. The CKMB concentration was measured using an IMx® automated immunodiagnostic analyzer (Abbott Laboratories, Abbott Park, Ill.). The assay used was the IMx®-CKMB assay (available as an assay kit from Abbott); a two-step sandwich assay using a solid phase anti-CKMB antibody and an anti-CKMM alkaline phosphatase conjugate. Table 3 illustrates the assay results as the percentage of the "day zero" CKMB concentration which remained in the matrixes over time. The assay results demonstrated that the CKMB stability was greatest in the reagent matrixes formulated in accordance with the invention containing either ATP or ADP, and that the stability was greater still in those matrixes which also included creatine.

TABLE 3

CKMB Stability with Creatine in the Reagent Matrix

| | | | CKMB Concentration (% of Day Zero Concentration) | | | |
|---|---|---|---|---|---|---|
| ATP | ADP | Creatine | Day 3 | Day 9 | Day 17 | Day 26 |
| no | no | no | 6 | 0 | 0 | 0 |
| yes | no | no | 79 | 51 | 33 | 20 |
| no | yes | no | 76 | 27 | 17 | 10 |
| yes | no | yes | 92 | 82 | 80 | 70 |
| no | yes | yes | 92 | 82 | 73 | 57 |

EXAMPLE 7

CKMB Stability with an Enzyme Activator

Multiple reagent matrix preparations of the invention were made substantially in accordance with the procedures described in Examples 1 and 2, i.e., the reagent lots contained normal human serum, ATP and creatine, and the lots differed only in that NAC was included or omitted. Various concentrations of CKMB isoenzyme were added to the individual reagent matrix preparations, and the preparations were then heat stressed at 37° C. over a period of eight days. The CKMB percent concentrations which remained over time were measured as described in Example 6. The results, presented in Table 4, demonstrated that the short-term high-temperature stability of the reagent matrix was increased with the addition of NAC to the matrix.

TABLE 4

CKMB Stability at 37° C. with NAC in the Reagent Matrix

| Sample No. | NAC | CKMB Concentration (% of Day Zero Concentration) | | | | |
|---|---|---|---|---|---|---|
| | | Day 1 | Day 2 | Day 3 | Day 4 | Day 8 |
| 1 | no | 34 | 21 | 13 | 0 | 5 |
| 2 | yes | 93 | 95 | 88 | 84 | 62 |
| 3 | yes | 96 | 91 | 91 | 86 | 71 |
| 4 | yes | 98 | 98 | 96 | 88 | 56 |
| 5 | yes | 79 | 68 | 62 | 47 | 29 |
| 6 | yes | 89 | 83 | 74 | 68 | 38 |

EXAMPLE 8

Assay Calibrators and Controls

Reagent matrixes were prepared substantially in accordance with the procedures described in Examples 1 through 5. Purified CKMB isoenzyme was then added in various amounts to produce CKMB assay calibrators which had final CKMB concentrations of 0.0, 3.0, 10.0, 30.0, 100.0 and 300.0 ng/ml. Purified CKMB isoenzyme was added in various amounts to produce CKMB assay controls which had final CKMB concentrations of 5.0, 20.0 and 120.0 ng/ml.

EXAMPLE 9

Comparison of CKMB Stability in Human, Animal and Synthetic Serum Media

Reagent matrixes were prepared substantially in accordance with the procedure described in Example 2, wherein NAC was omitted, and with the exception that the liquid medium used for a given matrix was selected from NHS, horse serum, goat serum or physiological diagnostic base. A given amount of CKMB isoenzyme was then added to each reagent matrix on day zero. Subsequent to storage at room temperature, the CKMB concentrations of the matrixes were periodically quantitated. The CKMB concentration was measured as described above in Example 6. Table 5 illustrates the measurement results as the percentage of the "day zero" CKMB concentration which remained in the matrixes over time. The assay results demonstrated that the reagent matrixes made with human, animal or artificial protein medium retained 82–100% of CKMB concentration even when stored for a period of 60 days at room temperature.

TABLE 5

CKMB Stability in Human, Animal and Synthetic Liquid Media
CKMB Concentration (% of Day Zero Concentration)

| Day | Human Serum | Goat Serum | Horse Serum | Physiological Diagnostic Base |
|---|---|---|---|---|
| 3 | 100 | 86 | 100 | 91 |
| 12 | 89 | 94 | 100 | 91 |
| 18 | 92 | 100 | 92 | 93 |
| 32 | 86 | 111 | 116 | 89 |
| 38 | 83 | 100 | 116 | 89 |
| 46 | 86 | 89 | 118 | 93 |
| 60 | 83 | 83 | 116 | 82 |

EXAMPLE 10

Phosphocreatine Stabilization of CKMB

Reagent matrixes B, D and H were prepared substantially in accordance with the procedures described in Example 2, 3 and 4, respectively. A stability study was then performed at room temperature to compare the stabilization effects of a substrate/substrate matrix (ATP plus creatine in matrix B), a product/substrate matrix (ADP plus creatine in matrix D) and a product/product matrix (ADP plus phosphocreatine in matrix H). In addition, comparison matrixes were made which contained either ADP or ATP alone (5 mM) in a normal human serum medium.

The CKMB concentrations were measured as described above in Example 6. Table 6 illustrates the measurement results as the percentage of the "day zero" CKMB concentration which remained in the matrixes over time. The assay results demonstrated that ATP alone provided greater stability than did ADP alone, and that the addition of creatine to either ATP or ADP provided increased stability. While the reagent matrix containing ADP and creatine phosphate provided the least stability, the enzyme stability obtained with the product/product matrix was substantially greater than that of the enzyme alone.

TABLE 6

CKMB Stabilization Study
CKMB Concentration (% of Day Zero Concentration)

| Day | ATP/ creatine | ADP/ creatine | ADP/ phosphocreatine | ADP | ATP |
|---|---|---|---|---|---|
| 0 | 100 | 100 | 100 | 100 | 100 |
| 1 | 96 | 98 | 104 | 98 | 94 |
| 4 | 93 | 95 | 88 | 89 | 93 |
| 7 | 94 | 91 | 82 | 91 | 94 |
| 11 | 101 | 93 | 77 | 90 | 92 |
| 18 | 91 | 85 | 53 | 74 | 91 |
| 27 | 91 | 81 | 38 | 65 | 79 |
| 35 | 89 | 76 | 29 | 60 | 79 |
| 49 | 87 | 75 | not measured | 52 | 71 |

Another study compared the stabilization effects of ATP/creatine, ATP/phosphocreatine and ADP/phosphocreatine reagent matrixes which were made according to the invention substantially following the procedures described in Examples 2, 3 and 4. The CKMB concentrations were measured as described above in Example 6. Table 7 illustrates the measurement results as the percentage of the "day zero" CKMB concentration which remained in the matrixes over time. These assay results demonstrated that the ATP/phosphocreatine and ADP/phosphocreatine reagent matrixes provided approximately the same stabilizing effect.

TABLE 7

CKMB Stabilization Study

| ATP | ADP | Creatine | Phospho-creatine | CKMB Concentration (% of day zero concentration) | | |
|---|---|---|---|---|---|---|
| | | | | Day 1 | Day 5 | Day 13 |
| yes | no | yes | no | 98 | 91 | 91 |
| yes | no | no | yes | 99 | 83 | 70 |
| no | yes | no | yes | 107 | 87 | 67 |

It will be appreciated by one skilled in the art that the use of enzyme products, enzyme substrates and combinations thereof is applicable to the stabilization of other enzymes or isoenzymes in accordance with the disclosure of the invention provided herein. Accordingly, the embodiments described and the preferred embodiments presented herein are intended as examples rather than as limitations. Thus, the description of the invention is not intended to limit the invention to the particular embodiments disclosed, but it is intended to encompass all equivalents and subject matter within the spirit and scope of the invention as described and as set forth in the following claims.

What is claimed is:

1. A liquid enzyme composition suitable for use as a calibrator or control reference reagent in an immunoassay for creatine kinase MB (CKMB) isoenzyme comprising
   1) a predetermined amount of isolated CKMB isoenzyme which is free of CKMM and CKBB isoenzymes and which is not bound to a carrier material;
   2) a CKMB stabilizer selected from the group consisting of:
      a) a substrate for CKMB isoenzyme selected from the group consisting of:
         i) adenosine triphosphate;
         ii) oxidized adenosine triphosphate;
         iii) adenosine trisposphate analogs;
         iv) oxidized adenosine triphosphate analogs;
         v) creatine; and
         vi) creatine analogs;
      b) a pair of products resulting from the action of CKMB isoenzyme on a substrate with one member selected from each group wherein
         i) one group consists of adenosine diphosphate, oxidized adenosine diphosphate, adenosine diphosphate analogs and oxidized adenosine diphosphate analogs; and
         ii) the other group consists of phosphocreatine, and phosphocreatine analogs;
      c) a combination of a CKMB isoenzyme substrate selected from group a hereinabove and of a CKMB isoenzyme product selected from Group b hereinabove;
      d) any of the stabilizers a through c and a CKMB isoenzyme activator selected from the group consisting of a sulfhydryl compound, a divalent metal ion and a combination thereof and
      e) combinations thereof; and
   3) a protein solution comprising human serum, animal serum or artificial serum said composition displaying less than a 10% loss of CKMB isoenzyme concentration after 27 days storage at room temperature, as measured by immunoassay.

2. A liquid enzyme composition suitable for use as a calibrator or control reference reagent in an immunoassay for creatine kinase MB (CKMB) isoenzyme formed by combining
   1) a predetermined amount of isolated CKMB isoenzyme which is free of CKMM and CKBB isoenzymes and is not bound to a carrier material;
   2) at least one CKMB substrate selected from the group consisting of oxidized adenosine triphosphate, adenosine triphosphate analogs, oxidized adenosine triphosphate analogs and creatine analogs; and
   3) a protein solution comprising human serum, animal serum or artificial serum said composition displaying less than a 10% loss of CKMB isoenzyme concentration after 27 days storage at room temperature as measured by immunoassay.

3. A liquid enzyme composition suitable for use as a calibrator or control reference reagent in an immunoassay for creatine kinase MB (CKMB) isoenzyme comprising
   1) a predetermined amount of isolated CKMB isoenzyme which is free of CKMM and CKBB isoenzymes and is not bound to a carrier material;
   2) a CKMB stabilizer selected from the group consisting of
      a) adenosine triphosphate;
      b) adenosine triphosphate and creatine;
      c) adenosine triphosphate and phosphocreatine;
      d) adenosine triphosphate and adenosine diphosphate;
      e) adenosine diphosphate and creatine;
      f) adenosine diphosphate and phosphocreatine;
      g) creatine and phosphocreatine;
      h) any of stabilizers a through g and an enzyme activator selected from the group consisting of:
         i) a sulfhydryl compound;
         ii) a divalent metal ion; and
         iii) a combination thereof;
      i) combinations thereof; and
   3) a protein solution comprising human serum, animal serum or artificial serum; said composition displaying less than a 10% loss of CKMB isoenzyme concentration after 27 days storage at room temperature as measured by immunoassay.

4. The liquid enzyme composition of claim 3 which comprises a CKMB activator selected from the group consisting of N-acetyl-cysteine and β-mercaptoethanol.

5. The liquid enzyme composition of claim 3 which comprises magnesium as a CKMB isoenzyme activator.

6. The liquid enzyme composition of claim 5 which comprises a CKMB activator selected from the group consisting of N-acetyl-cysteine and β-mercaptoethanol.

7. The liquid enzyme composition of claim 1 or 3 wherein the protein solution is heat-inactivated alkaline-shocked human serum.

8. The liquid enzyme composition of claim 3 wherein the CKMB stabilizer comprises adenosine triphosphate and creatine.

9. The liquid enzyme composition of claim 8 wherein the adenosine triphosphate concentration is between about 0.5 and 50 mM and the creatine concentration is between 5 and 160 mM when the composition is initially formed.

10. The liquid enzyme composition of claim 8 wherein the CKMB stabilizer further comprises a CKMB isoenzyme activator selected from the group consisting of N-acetyl-cysteine and β-mercaptoethanol.

* * * * *